(12) United States Patent
Kwiatkowski

(10) Patent No.: US 7,118,864 B2
(45) Date of Patent: Oct. 10, 2006

(54) AMPLIFIABLE PROBE

(75) Inventor: Marek Kwiatkowski, Uppsala (SE)

(73) Assignee: Quiatech AB, Uppsala (SE)

( * ) Notice: Subject to any disclaimer, the term of this patent is extended or adjusted under 35 U.S.C. 154(b) by 489 days.

(21) Appl. No.: 10/143,496

(22) Filed: May 9, 2002

(65) Prior Publication Data

US 2003/0003483 A1    Jan. 2, 2003

Related U.S. Application Data

(60) Provisional application No. 60/298,767, filed on Jun. 15, 2001.

(51) Int. Cl.
*C12Q 1/68* (2006.01)
*C12P 19/34* (2006.01)

(52) U.S. Cl. .......................................... 435/6; 435/91.2

(58) Field of Classification Search ............... 435/91.1, 435/91.2, 6; 536/24.33
See application file for complete search history.

(56) References Cited

U.S. PATENT DOCUMENTS

| | | | |
|---|---|---|---|
| 4,882,269 A | 11/1989 | Schneider et al. | |
| 5,462,854 A | 10/1995 | Coassin et al. | |
| 5,665,539 A | 9/1997 | Sano et al. | |
| 5,683,869 A * | 11/1997 | Ramsay Shaw et al. | 435/6 |
| 5,708,154 A | 1/1998 | Smith et al. | |
| 5,747,255 A | 5/1998 | Brenner | |
| 5,834,202 A | 11/1998 | Auerbach | |
| 5,849,481 A | 12/1998 | Urdea et al. | |
| 5,912,124 A | 6/1999 | Kumar | |
| 5,917,031 A | 6/1999 | Miura et al. | |
| 6,030,581 A | 2/2000 | Virtanen | |
| 6,087,133 A | 7/2000 | Dattagupta et al. | |

FOREIGN PATENT DOCUMENTS

| | | |
|---|---|---|
| EP | 0 204 510 A2 | 12/1986 |
| EP | 0 427 074 A2 | 5/1991 |
| EP | 0 566 751 A1 | 10/1993 |
| WO | WO 92/06985 | 4/1992 |
| WO | WO 98/51698 | 11/1998 |
| WO | WO 99/49079 | 9/1999 |
| WO | WO 99/66071 * | 12/1999 |
| WO | WO 00/36141 | 6/2000 |

OTHER PUBLICATIONS

Schweitzer et al. Immunoassays with rolling circle DNA amplification: A versatile platform for ultrasensitive antigen detection. Aug. 29, 2000. PNAS vol. 97:10113-10119.*

Capaldi et al., "Signal amplification through nucleotide extension and excision on a dendritic DNA platform," *Nucl. Acids Res.*, 2000, 28(7):i-viii.

de Silva and Wittwer, "Monitoring hybridization during polymerase chain reaction," *J. Chromatography B*, 2000, 741:3-13.

Horn and Urdea, "Forks and combs and DNA: the synthesis of branched oligodeoxyribonucleotides," *Nucl. Acids Res.*, 1989, 17(17):6959-6967.

Mitra and Church, "*In situ* localized amplification and contact replication of many individual DNA molecules," *Nucl. Acids Res.*, 1999, 27(24):i-vi.

Nilsson et al., "Padlock Probes: Circularizing Oligonucleotides for Localized DNA Detection," *Science*, 1994, 265:2085-2088.

Notomi et al., "Loop-mediated isothermal amplification of DNA," *Nucl. Acids Res.*, 2000, 28(12):i-vii.

Ogata and Miura, "Genetic information 'created' by archaebacterial DNA polymerase," *Biochem. J.*, 1997, 324:667-671.

Ogata and Miura, "Creation of genetic information by DNA polymerase of the archaeon *Thermococcus litoralis*: influences of temperature and ionic strength," *Nucl. Acids Res.*, 1998, 26(20):4652-4656.

Ogata and Miura, "Creation of genetic information by DNA polymerase of the thermophilic bacterium *Thermus thermophilus*," *Nucl. Acids Res.*, 1998, 26(20):4657-4661.

Ogata and Miura, "Elongation of Tandem Repetitive DNA by the DNA Polymerase of the Hyperthermophilic Archaeon *Thermococcus litoralis* at a Hairpin—Coil Transitional State: A Model of Amplification of a Primordial Simple DNA Sequence," *Biochemistry*, 2000, 39:13993-14001.

Ogata and Morino, "Elongation of repetitive DNA by DNA polymerase from a hyperthermophilic bacterium *Thermus thermophilus*," *Nucl. Acids Res.*, 2000, 28(20):3999-4004.

Schweitzer et al., "Immunoassays with rolling circle DNA amplification: A versatile platform for ultrasensitive antigen detection," *Proc. Natl. Acad. Sci. USA*, 2000, 97(18):10113-10119.

Sims et al., "Immunopolymerase Chain Reaction Using Real-Time Polymerase Chain Reaction for Detection," *Analytical Biochemistry*, 2000, 281:230-232.

* cited by examiner

*Primary Examiner*—Jeffrey Fredman
*Assistant Examiner*—Heather G. Calamita
(74) *Attorney, Agent, or Firm*—Fish & Richardson P.C.

(57) ABSTRACT

Synthetic probes and methods for detecting analytes using such probes are described. The probes contain an analyte reactive moiety linked to a nucleic acid molecule that can be extended by DNA polymerase.

18 Claims, 4 Drawing Sheets

AMPLIFIABLE PROBE

RELATED APPLICATIONS

This application claims the benefit of prior U.S. provisional application 60/298,767, filed Jun. 15, 2001.

TECHNICAL FIELD

The invention relates to methods and materials for detecting analytes. More specifically, the invention relates to amplifiable probes and methods for detecting analytes such as nucleic acids and polypeptides.

BACKGROUND

Analyte binding assays are useful for detecting a variety of analytes in research and clinical laboratories. Immunoassays, in many different formats, have been used to detect analytes such as viral and bacterial antigens, immunoglobulins, hormones, cell subtypes, pharmaceuticals, drugs of abuse, and toxins. Immunoassays involve the formation of a complex between an antigenic substance and an antibody. Typically, either a component of the complex or a competing antigen is labeled with either a radioisotope or a fluorescent label to allow quantitative or qualitative analyte detection. Although the sensitivity of immunoassays has been enhanced by enzyme-mediated amplification schemes, wherein a secondary signal-generating enzyme system is coupled to an enzyme/antibody conjugate, further increases in sensitivity would enhance the ability to detect analytes.

Nucleic acid hybridization assays have been used to detect specific nucleic acid analytes. Nucleic acid hybridization assays involve the formation of a complex between a target nucleic acid and a complementary probe nucleic acid. Typically, the probe nucleic acid is labeled with either a radioisotope or a fluorescent label to allow quantitative or qualitative detection of the target nucleic acid analyte. The sensitivity of nucleic acid hybridization assays has been enhanced through the use of a probe nucleic acid having a polymeric tail that is bound by a secondary signal-generating probe (see e.g., U.S. Pat. No. 4,882,269). The sensitivity of nucleic acid hybridization assays also has been enhanced by procedures that incorporate additional sites for attachment of a signal-emitting secondary probe to the hybridized probe nucleic acid (see e.g., WO 89/03891 and European Patent Application 204510). Sensitivity, however, is limited by the nature of the labels. Thus, a need exists for a more sensitive method for detecting analytes.

SUMMARY

The invention is based on a new class of amplifiable probes that can be used in a variety of diagnostic applications to detect, for example, the presence or absence of disease-relevant molecules or genetic loci. An amplifiable probe includes a signal-generating nucleic acid and a molecule that binds to, or that can be modified by, an analyte. Analytes can be detected in situ by amplification of an analyte-reacted probe.

In one aspect, the invention features an amplifiable probe that includes an analyte reactive moiety, at least one signal-generating nucleic acid, wherein each at least one signal-generating nucleic acid further includes at least one self-complementary unit, wherein each at least one self-complementary unit includes a first sequence element and a second sequence element, and wherein the first and the second sequence elements are complementary, and one or more linkers that connect the analyte reactive moiety to the at least one signal-generating nucleic acid. The signal-generating nucleic acid can be extendable and can have two or more 3' ends. The analyte reactive moiety can be a polypeptide or a nucleic acid molecule, and can interact with one or more polypeptides or one or more nucleic acid molecules. For example, the analyte reactive moiety can interact with one or more molecules selected from the group consisting of polypeptide, nucleic acid, carbohydrate, lipid, and hapten.

An intervening sequence element can be between the first and the second sequence elements of at least one self-complementary unit, wherein the intervening sequence element is not complementary to the first or the second sequence elements of the at least one self-complementary unit. The at least one signal-generating nucleic acid may contain at least two self-complementary units, wherein an intervening sequence element is between at least two of the self-complementary units, and wherein the intervening sequence element is not complementary to the first or the second nucleotide sequence elements of the at least two self-complementary units.

The invention also features a method of detecting the presence or absence of an analyte in a sample. The method includes contacting the sample with an amplifiable probe under conditions whereby the analyte, if present, binds the amplifiable probe to form a probe/analyte complex. The amplifiable probe includes an analyte reactive moiety, at least one extendable signal-generating nucleic acid, wherein each at least one extendable signal-generating nucleic acid further includes at least one self-complementary unit, wherein each self-complementary unit includes a first sequence element and a second sequence element, and wherein the first and the second nucleotide sequence elements are complementary, and one or more linkers that connect the analyte reactive moiety to the at least one signal-generating nucleic acid. The method further includes extending the at least one extendable signal-generating nucleic acid in a reaction mixture that includes probe/analyte complex, e.g, isothermally or by performing at least one cycle of extension, and detecting the presence or absence of the extended signal-generating nucleic acid, wherein presence of the extended signal-generating nucleic acid correlates with the presence of the analyte. Two or more cycles of extension can be performed. The reaction mixture further can include at least one nucleotide triphosphate that is detectably labeled, e.g., with a radioisotope, non-radioactive dye, or a non-radioactive label such as a fluorescent label. The reaction mixture further can include an isolated nucleic acid template, the nucleic acid template including at least one self-complementary unit, wherein each self-complementary unit incudes a first hybridizing sequence element and a second hybridizing sequence element, wherein the first and the second hybridizing sequence elements are complementary to each other, and wherein the nucleic acid template is blocked at its 3' and 5' termini. The isolated nucleic acid template can include a phosphorothioate backbone.

In another aspect, the invention features a method of detecting the presence or absence of an analyte in a sample. The method includes contacting the sample with an amplifiable probe under conditions whereby the analyte, if present, reacts with the amplifiable probe to form a modified amplifiable probe. The amplifiable probe can include an analyte reactive moiety, at least one extendable signal-generating nucleic acid, wherein each at least one extendable signal-generating nucleic acid further includes at least one self-complementary unit, wherein each self-complementary unit includes a first sequence element and a second sequence element, and wherein the first and second sequence elements are complementary, and one or more linkers that connect the analyte reactive moiety to the at least one signal-generating nucleic acid. The method further includes extending the at least one extendable signal-generating nucleic acid in a reaction mixture that includes the modified amplifiable probe, and detecting the presence or absence of the extended signal-generating nucleic acid, wherein presence of the extended signal-generating nucleic acid correlates with the presence of the analyte. The extendable signal-generating nucleic acid can be extended by isothermal extension or by performing at least one cycle of extension (e.g., two or more cycles of extension).

In yet another aspect, the invention features an isolated nucleic acid template that includes at least one self-complementary unit, wherein each self-complementary unit includes a first hybridizing sequence element and a second hybridizing sequence element, wherein the first and second hybridizing sequence elements are complementary to each other, and wherein the nucleic acid template is blocked at its 3' terminus. The nucleic acid template can include a phosphorothioate backbone and can be blocked at its 3' and 5' termini. An intervening sequence element can be between the first and second hybridizing sequence elements of at least one said self-complementary unit, and wherein the intervening sequence element is not complementary to the first or second hybridizing sequence elements of the at least one self-complementary unit. The nucleic acid template can contain at least two self-complementary units, wherein an intervening sequence element is between at least two of the self-complementary units, and wherein the intervening sequence element is not complementary to the first or second hybridizing sequence elements of the at least two self-complementary units.

The invention also features an amplifiable complex that includes an amplifiable probe and an isolated nucleic acid template, wherein the isolated nucleic acid template is hybridized to the at least one extendable signal-generating nucleic acid of the amplifiable probe. The amplifiable probe includes an analyte reactive moiety, at least one extendable signal-generating nucleic acid, wherein each extendable signal-generating nucleic acid further includes at least one self-complementary unit, wherein each self-complementary unit includes a first sequence element and a second sequence element, and wherein the first and second sequence elements are complementary; and one or more linkers that connect the analyte reactive moiety to the at least one signal-generating nucleic acid. The isolated nucleic acid template includes at least one self-complementary unit, wherein each self-complementary unit includes a first hybridizing sequence element and a second hybridizing sequence element, wherein the first and second hybridizing sequence elements are complementary, and wherein the nucleic acid template is blocked at its 3' and 5' termini. The analyte reactive moiety can be bound to an analyte.

In yet another aspect, the invention features a method of detecting the presence or absence of an analyte in a sample. The method includes contacting the sample with an amplifiable probe under conditions whereby the analyte, if present, binds the amplifiable probe to form a probe/analyte complex, the amplifiable probe including an analyte reactive moiety, at least one signal-generating nucleic acid, wherein each at least one signal-generating nucleic acid further includes at least one self-complementary unit, wherein each self-complementary unit includes a first sequence element and a second sequence element, and wherein the first and the second nucleotide sequence elements are complementary, and one or more linkers that connect the analyte reactive moiety to the at least one signal-generating nucleic acid. The method further includes contacting the probe/analyte complex with a cognate nucleic acid template, extending the cognate nucleic acid template by performing an isothermal amplification reaction in a reaction mixture that includes the probe-analyte complex, and detecting the presence or absence of the extended signal-generating nucleic acid, wherein presence of the extended signal-generating nucleic acid correlates with the presence of the analyte. The signal-generating nucleic acid can be extendable.

The invention also features a kit that includes an amplifiable probe as described above. The kit further can include a blocked template, the blocked template including at least one self-complementary unit, wherein each self-complementary unit includes a first hybridizing sequence element and a second hybridizing sequence element, wherein the first and second hybridizing sequence elements are complementary, and wherein the nucleic acid template is blocked at its 3' and 5' termini. The signal-generating nucleic acid can be extendable. The kit further can include a cognate nucleic acid primer, the cognate nucleic acid primer including a hybridizing sequence element that is complementary to a sequence element on the signal generating molecule.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
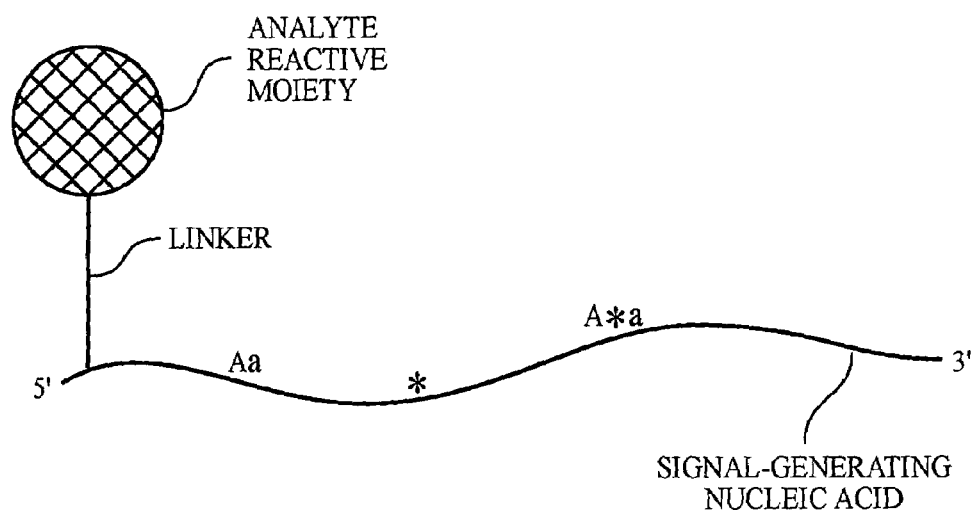
FIG. 1 is a schematic diagram of a representative amplifiable probe.

In general, the invention provides amplifiable probes that can be used to detect analytes. An amplifiable probe includes an analyte reactive component and a signal-generating nucleic acid. An analyte-reacted amplifiable probe is detected by amplifying a signal-generating nucleic acid. "Amplifying" refers to increasing the length of a signal-generating nucleic acid either by extending the signal-generating nucleic acid (i.e., localized amplification) or by extending a cognate nucleic acid primer (i.e., non-localized amplification). Amplification of an analyte-reacted amplifiable probe provides a very sensitive method to visualize analytes in situ.

Amplifiable Probes

Amplifiable probes of the invention contain an analyte reactive moiety, a signal-generating nucleic acid, and a linker that connects the analyte reactive moiety to the signal-generating nucleic acid. The term "analyte reactive moiety" refers to a molecule that reacts with an analyte to produce an amplifiable probe/analyte complex, or reacts with an analyte to produce a chemically or enzymatically modified analyte reactive moiety. Modification of an analyte reactive moiety can include, for example, addition of atoms or chemical groups, deletion of atoms or chemical groups, cleavage, ligation, and truncation. An analyte reactive moiety can be, for example, a polypeptide, nucleic acid, carbohydrate, lipid, or small molecule. Thus, probe/analyte complexes that can be formed include, for example, polypeptide-polypeptide, polypeptide-nucleic acid, nucleic acid-nucleic acid, and polypeptide-small molecule complexes. The term "small molecule" refers to any organic molecule weighing less than 1000 daltons. The term "polypeptide" refers to any chain of at least five amino acids and can include, without limitation, all or part of an antibody, antigen, enzyme, or enzyme substrate. The term "nucleic acid" refers to any chain of at least 10 nucleotides, whether naturally occurring or synthetic. A naturally occurring nucleic acid is "isolated" if it is free of sequences that are normally adjacent to one or both ends of the nucleic acid molecule in a naturally occurring genome. A synthetic nucleic acid is "isolated" if it separated from the components of a synthesis reaction. Nucleic acid analyte reactive moieties include, without limitation, DNA or RNA (e.g., cDNA, mRNA, rRNA, and tRNA). Padlock probes are particularly useful analyte reactive moieties.

Padlock probes are linear oligonucleotides that generally contain nucleotide sequences complementary to a target sequence at the 5' and 3' ends of the oligonucleotide and non-target sequences in the middle portion of the oligonucleotide. The sequences complementary to a target sequence can hybridize to the target sequence, bringing the ends of the oligonucleotides together, which can be ligated to produce a circular probe. See, Nilsson et al., *Science*, 265:2085–2088 (1994) and WO 99/49079 for a description of padlock probes.

A signal-generating nucleic acid has at least one self-complementary unit. A "self-complementary unit" is a nucleic acid segment that contains two complementary sequence elements (i.e., two sequence elements that are complementary to each other). Each complementary sequence element is a contiguous stretch of nucleotides that can be from about 2 to about 400 nucleotides in length (e.g., 2 to 10 nucleotides, 10 to 20 nucleotides, 20 to 40 nucleotides, 40 to 60 nucleotides, 60 to 80 nucleotides, 80 to 100 nucleotides, 100 to 150 nucleotides, 150 to 200 nucleotides, 200 to 300 nucleotides, 300 to 400 nucleotides). The GC content of the complementary sequence unit can range from about 20% to 60%, e.g., about 25 to 50%. Exemplary self-complementary units include, in 5' to 3' orientation: AT/AT, AA/TT, AC/GT, ATA/TAT, ACT/AGT, AGCT/AGCT, TCAG/CTGA, TACATGTA/TACATGTA, and AGATATCT/AGATATCT. Signal-generating nucleic acids having the palindromic sequences $(AGATATCT)_6$ or $(TACATGTA)_6$ are particularly useful. See, for example, Ogata and Morino, *Nucleic Acids Res.*, 28(20):3999–4004 (2000); and Ogata and Miura, *Biochemistry*, 39:13993–14001 (2000).

The complementary sequence elements of a self-complementary unit need not be strictly complementary (i.e., complementary at each sequence position). Rather, the complementary sequence elements of a self-complementary unit must be able to hybridize to each other. To determine if complementary sequence elements can hybridize to each other, two oligonucleotides are synthesized, one containing only the first complementary sequence element and the other containing only the second complementary sequence element. Hybridization of the two oligonucleotides is assessed under conditions of moderate to high stringency. Moderately stringent hybridization conditions include hybridization at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1–15 ng/mL probe (about $5\times10^7$ cpm/µg), and wash steps at about 50° C. with a wash solution containing 2×SSC and 0.1% SDS. For high stringency, the same hybridization conditions can be used, but washes are performed at about 65° C. with a wash solution containing 0.2×SSC and 0.1% SDS. Accordingly, the length and degree of complementarity of sequence elements in a self-complementary unit can vary within the bounds defined by these stringent hybridization conditions. In general, self-complementary units made up of relatively long complementary sequence elements can contain more mismatches between the complementary sequence elements and still hybridize to each other under stringent conditions. Self-complementary units made up of relatively short complementary sequence elements are generally less tolerant of mismatches between the complementary sequence elements.

A signal-generating nucleic acid can contain a single self-complementary unit, Aa, wherein the italicized letter pair represents a self-complementary unit, and the upper case letter represents a sequence element that is complementary to that represented by the corresponding lower case letter (see FIG. 1). Alternatively, a signal-generating nucleic acid can contain multiple self-complementary units, including identical self-complementary units (e.g., Aa, Aa, Aa), different self-complementary units (e.g, Aa, Bb, Cc), or a mixture of identical and different self-complementary units (e.g., Aa, Bb, Aa). The signal-generating nucleic acid need not have a strictly pairwise relationship of complementary sequence elements.

A signal-generating nucleic acid can contain intervening sequence elements that are not complementary to the complementary sequence elements (see FIG. 1). Intervening sequence elements can be present anywhere on the signal-generating nucleic acid, including between self-complementary units (e.g., Aa*Aa), adjacent to a self-complementary unit (e.g., *Aa), and between complementary sequence elements (e.g., A*a), where * denotes an intervening sequence element. Intervening sequence elements can range in length from 1 nucleotide to about 1000 nucleotides, e.g., 1 to 10 nucleotides, 10 to 20 nucleotides, 20 to 40 nucleotides, 40 to 60 nucleotides, 60 to 80 nucleotides, 80 to 100 nucleotides, 100 to 150 nucleotides, 150 to 200 nucleotides, 200 to 400 nucleotides, 400 to 600 nucleotides, 600 to 800 nucleotides, or 800 to 1000 nucleotides.

Typically, a signal-generating element is extendable. The term "extendable" as used herein refers to a nucleic acid having at least one free 3' terminus that can be extended by DNA polymerase. An extendable signal-generating nucleic acid can have a single free 3' terminus or can have two or more free 3' termini. Such nucleic acids can be synthesized using known methodologies, including automated DNA synthesis in the 3' to 5' direction using phosphoramidite technology. A second free 3' terminus can be introduced by continuing synthesis in the 5' to 3' direction using inverted amidite technology, where the amidite function is located at the 5' position. Inverted amidites are available commercially from, for example, Glen Research (Sterling, Va.). Alternatively, a second free 3' end can be introduced by conjugating a nucleic acid that is modified at its 5' end. Two 5'-thiolated nucleic acids also can be oxidized to form a disulfide-linked nucleic acid having two free 3' termini. A branched type of oligonucleotide having several 3'-ends can be synthesized by a procedure similar to that of Horn and Urdea, *Nucleic Acids Res.*, 17:6959–6967 (1989) or U.S. Pat. No. 5,849, 481. Alternatively, post-synthetic coupling of an oligonucleotide to a separately prepared branched linking molecule can be used for the same purpose.

Signal-generating nucleic acids typically range in length from about 20 nucleotides to about 1000 nucleotides (e.g., 20–80 nucleotides, 20–60 nucleotides, 24 to 48 nucleotides, 30–70 nucleotides, 40–65 nucleotides, 50–100 nucleotides, 100–200 nucleotides, 200–400 nucleotides, 400–600 nucleotides, 600–800 nucleotides, or 800–1000 nucleotides). The length of an extendable signal-generating molecule can be considerably greater after amplification.

Signal-generating nucleic acids can be connected to an analyte reactive moiety by a linker. The term "linker" refers to any molecule that can connect an analyte reactive moiety to a signal-generating nucleic acid, either covalently or non-covalently. Thus, suitable linkers have at least one functional group that can connect to an analyte reactive moiety and at least one functional group that can connect to a signal-generating nucleic acid. The type of linker that is used depends on the nature of the functional groups present on the analyte reactive moiety and signal-generating nucleic acid.

A linker, or a part of a linking function, may be incorporated into the signal-generating nucleic acid during its chemical synthesis. For example, during chemical synthesis of an extendable signal-generating nucleic acid having two 3' ends, a modified central nucleotide can be incorporated as the last amidite during synthesis in the 3' to 5' direction. The extendable signal-generating nucleic acid can be connected to the analyte reactive moiety via function R (see Formula 1, where (1) represents an oligonucleotide synthesized in the 3' to 5' direction; (2) represents an oligonucleotide synthesized in the 5' to 3' direction; and R represents a hapten such as biotin, digoxin, dinitrophenol, or a reactive function (e.g., a nucleophile such as an amino, thiol, or carboxyl).

Formula 1

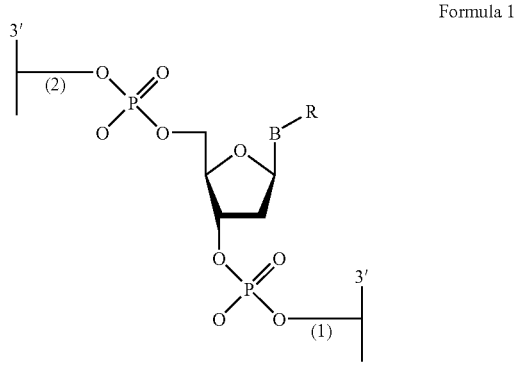

If necessary, the central nucleotide can be separated from both oligonucleotides by a linker that does not have a nucleotidic character. The central building block can be a derivative of a nucleoside (B typically is dU or dC) or a trifunctional compound that is not a nucleoside. An example of a trifunctional compound is provided in formula 2.

Such building blocks are available commercially from, for example, Glen Research, Sterling, Va. (catalog #10-1038-90 for biotin, catalog #10-1037-02 for amine, and catalog #10-1035002 for carboxy). After incorporation of the central building block, synthesis can be continued in the 5' to 3' direction. Alternatively, a standard 5' amino modifier amidite can be incorporated into the extendable nucleic acid molecule, followed by activation by succinimidyl 3-(2-pyridyldithio)propionate (SPDP) and conjugation to a 5'-thiol derivatized nucleic acid molecule. In either case, an extendable signal-generating nucleic acid having two 3' ends is produced, which can be connected to an analyte reactive moiety via the hapten or reactive function (R in formula 1).

A linker can connect to one or more signal-generating nucleic acids, or analyte reactive moieties, derivatized with an amino, hydroxylamino, or hydrazo function via an aldehyde functional group on the linker. An aldehyde function can be introduced into the linker with a specific reagent (e.g., succinimidyl 4-formylbenzoate (Molecular Probes, Inc., Eugene, Oreg.) or by oxidative periodate cleavage of diols such as sugars. A linker can connect to a thiolated signal-generating nucleic acid or thiolated analyte reactive moiety via an iodoacetamido, bromoacetamido, maleimido, or pyridyldithio functional group on the linker.

Linkers can connect one or more signal-generating nucleic acids to one or more analyte reactive moieties (i.e., one signal-generating nucleic acid to one analyte reactive moiety, one signal-generating nucleic acid to multiple analyte reactive moieties, multiple signal-generating nucleic acids to one analyte reactive moiety, or multiple signal-generating nucleic acids to multiple analyte reactive moieties). For example, multiple signal-generating nucleic acids can be joined by introduction of a linker containing multiple amino functions. Amines can be conjugated to a signal-generating nucleic acid either directly (e.g., amine-carboxyl or amine-oligonucleotide-5'-monophosphate) or indirectly by reaction of the amino group with a reagent that introduces a function such as an aldehyde, dithiopyridyl, or maleimido and reaction with a suitably 5'-modified nucleic acid molecule. Analyte reactive moieties also can be connected to a signal-generating nucleic acid by cross-linkers such as succinimidyl iodoacetate, succinimidyl 6-maleimidylhexanoate, or N-((2-pyridyldithio)ethyl)-4-azidosalicylamide (Molecular Probes, Inc., Eugene, Oreg.). A nucleic acid analyte reactive moiety is typically connected to a signal-generating nucleic acid by a non-nucleotidic linker.

Formula 2

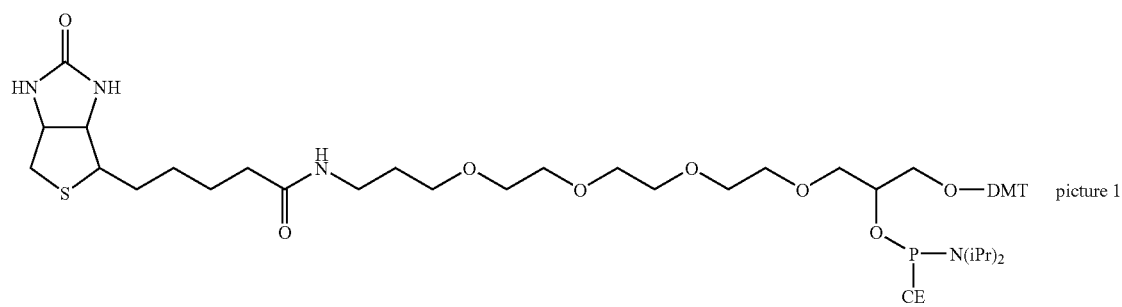

picture 1

Methods of Detecting an Analyte

Amplifiable probes of the present invention can be used to detect the presence or absence of an analyte in a biological sample such as blood, plasma, serum, urine, saliva, sputum, cerebrospinal fluid, or tissue, or in a nucleic acid or polypeptide array. Amplifiable probes are particularly useful for localized in situ detection of analytes (e.g., on a microscopic slide containing a fixed sample or a two-dimensional gel-electrophoretic plate). Typically, the method for detecting analytes includes contacting an amplifiable probe with a sample; extending the nucleic acid molecule of an amplifiable probe; and detecting the extended nucleic acid molecule of an amplified probe. Analytes typically are immobilized (i.e., spatially restrained) prior to the contacting step using known methodologies. Analytes can be immobilized using, for example, an analyte-attractive solid surface (e.g., filter or glass slide), an analyte-binding bioreactor (e.g., affinity column), an ordered liquid or solid phase array (e.g., nucleic acid or polypeptide chips, integrated biocompact disc (see U.S. Pat. No. 6,030,581), or microtiter dish), gel electrophoresis, or thin layer chromatography. Arrays, such as high-density oligonucleotide arrays are available commercially from, for example, Affymetrix (Santa Clara, Calif.). In addition, see WO 98/57698 for arrays of inverted oligonucleotides. Analytes also can be in solution during the contacting step.

The contacting step is performed under conditions so that the analyte, if present in the sample, reacts with the analyte reactive moiety of an amplifiable probe to form either a probe/analyte complex or a modified probe. The analyte reactive moiety of an amplifiable probe can be chemically or enzymatically modified following the reaction with an analyte by, for example, addition of atoms or chemical groups, deletion of atoms or chemical groups, ligation, cleavage, or truncation. For example, an amplifiable probe that contains an oligonucleotide as the analyte reactive moiety linked non-nucleotidically to a signal-generating nucleic acid can be used in an oligonucleotide ligation assay (OLA). In this assay, the analyte reactive moiety of the amplifiable probe can hybridize to a target nucleic acid, along with a second oligonucleotide that is part of an oligonucleotide array. In the presence of the complementary target sequence, the analyte reactive moiety of the amplifiable probe and the second oligonucleotide of the array can be ligated by a ligase, which covalently immobilizes the amplifiable probe to the solid phase. Extension of the signal-generating nucleic acid will produce a signal at a specific site on the array. Suitable contacting step conditions will vary depending on the type of analyte reactive moiety that is being used.

Unreacted probes can be separated from reacted probes before amplification, or between the amplification and detection steps. For example, probe/analyte complexes can be separated from unbound probes by washing unbound probes from immobilized probe/analyte complexes. When the analyte is not immobilized prior to the contacting step, reacted probes can be separated from unreacted probes by electrophoresis or immunoaffinity purification using an anti-analyte antibody (e.g., an antibody specific for an epitope on the analyte not bound to analyte reactive moiety) or an antibody that selectively binds either bound or unbound analyte reactive moieties. The reacted probe/analyte complex then can be immobilized as described above for analytes. Similarly, modified probes can be separated from unmodified probes by immunoaffinity purification using an antibody that selectively binds either modified or unmodified analyte reactive moieties. Modified probes containing a nucleic acid analyte reactive moiety can be separated from unmodified probes by differential hybridization using an immobilized nucleic acid template under conditions that permit hybridization to either modified or unmodified analyte reactive moieties.

Reacted probes can be amplified via at least one cycle of extension (e.g., two or more cycles) that includes 1) thermally denaturing an extendable signal-generating nucleic acid, 2) annealing of complementary sequence elements at a lower temperature, and 3) extending the extendable signal-generating nucleic acid in the 5' to 3' direction with a DNA polymerase. Alternatively, the signal-generating nucleic acid can be isothermally extended with a DNA polymerase. Suitable DNA polymerases are resistant to inactivation at temperatures greater than 60° C., and include commercially available DNA polymerases from, for example, *Thermococcus litoralis* (Vent® DNA polymerase, New England Biolabs), *T. thermophilus* (Ampli Taq® DNA polymerase, Perkin Elmer), and *T. flavus* (Tfl DNA polymerase, Promega, Wis.). Typically, an extension reaction contains approximately 200 µM of each deoxynucleotide triphosphate and approximately 25 U/ml of DNA polymerase. Suitable buffers for extension reactions are supplied with commercially available polymerases.

Figure 2A:
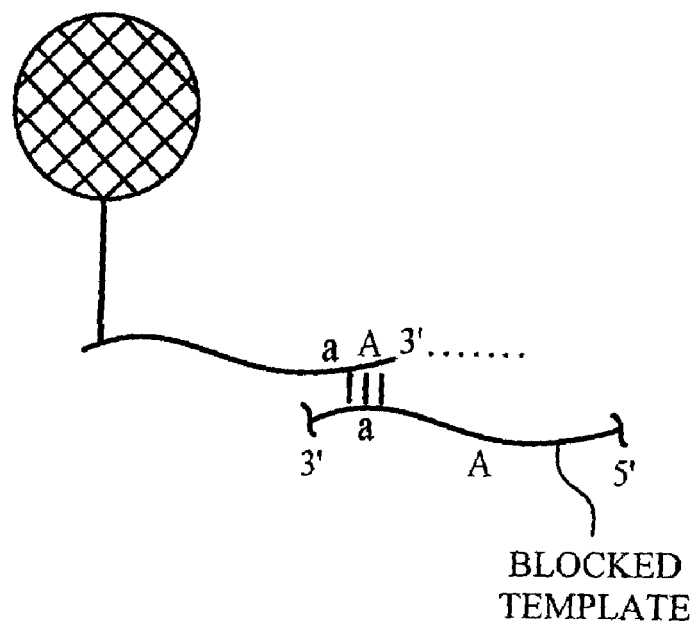
FIGS. 2A–2D are schematic diagrams of different modes of extending a nucleic acid molecule.

An isolated nucleic acid template can be included in the reaction, and is referred to as a "blocked template." A blocked template contains at least one self-complementary unit composed of hybridizing sequence elements that are complementary to each other and to at least one sequence element present on the extendable signal-generating nucleic acid. To prevent extension and exonucleotidic degradation of the template, it is blocked at its 3' terminus or both the 5' and 3' termini with, for example, phosphate residues, oligoethyleneglycol residues, or non-nucleotide amidite units. Endonucleotidic degradation of both the amplified probe and exogenous template also can be prevented by using an exogenous nucleic acid template with a phosphorothioate backbone and by using nucleotide thiotriphosphates for enzymatic extension of the amplified probe. When a blocked template is present in the extension reaction, sequence elements within the extendable signal-generating nucleic acid can anneal to the hybridizing sequence elements on the blocked template, which serve as a template for 5' to 3' extension by DNA polymerase (See FIG. 2A). Thus, after a round of amplification, the extendable signal-generating nucleic acid is elongated, with the newly added nucleotides having a sequence complementary to the blocked template.

Figure 2B:
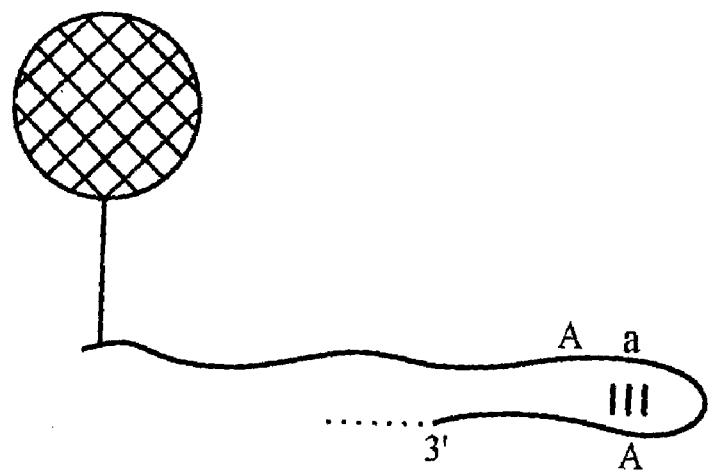
Figure 2C:
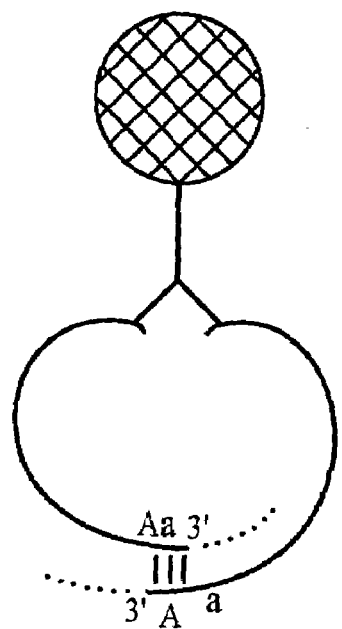
Figure 2D:
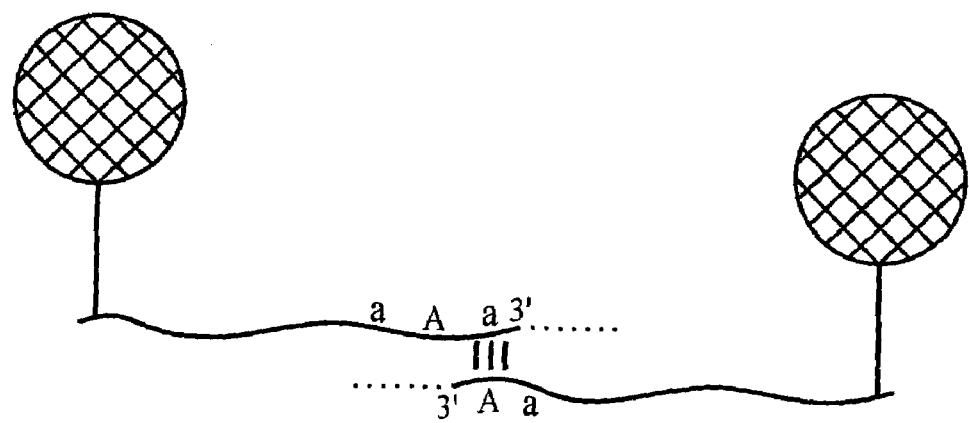

An extendable signal-generating nucleic acid can also serve as its own template. Thus, amplification can include intramolecularly templated extension following annealing of an extendable signal-generating nucleic acid to itself (See FIG. 2B). In this mode of amplification, complementary sequence elements within a single extendable signal-generating nucleic acid anneal to each other after thermal denaturation, and serve as a template for 5' to 3' extension by DNA polymerase. Amplification also can involve intermolecularly templated extension following annealing of an extendable signal-generating nucleic acid to a second signal-generating nucleic acid connected to the same analyte reactive moiety (See FIG. 2C). In embodiments in which the second signal-generating nucleic acid is also extendable, complementary sequence elements within the signal-generating nucleic acids can anneal to each other after thermal denaturation, and one or both signal-generating nucleic acids can serve as a template for 5' to 3' extension by DNA polymerase. Intermolecularly templated extension also can occur following annealing of an extendable signal-generating nucleic acid to a signal-generating nucleic acid connected to a different amplifiable probe (See FIG. 2D). In embodiments in which the signal-generating nucleic acids on each probe are extendable, complementary sequence elements within two different signal-generating nucleic acids connected to different analyte reactive moieties can anneal to each other after thermal denaturation, and one or both signal-generating nucleic acids can serve as a template for 5' to 3' extension by DNA polymerase. Hybridization conditions can be modified to manipulate the frequency with which a particular mode of amplification occurs.

Figure 3A:
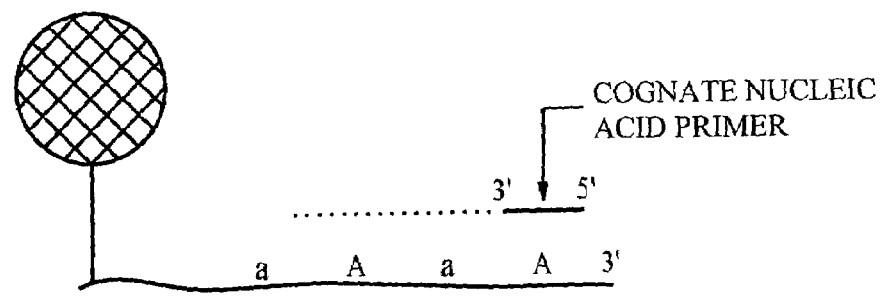
FIGS. 3A–3C are schematic diagrams of non-localized amplification.
Figure 3B:
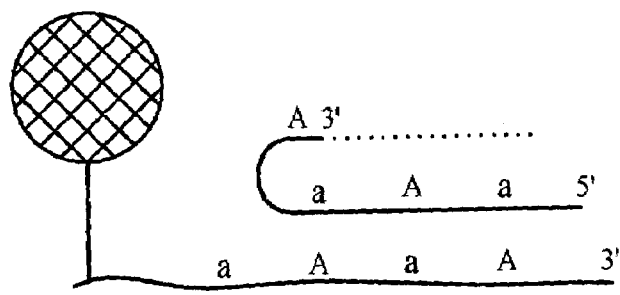
Figure 3C:
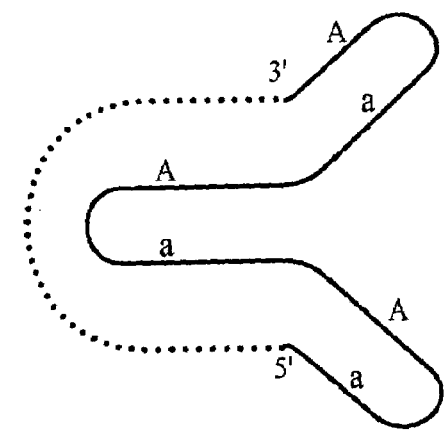

Reacted amplifiable probes also can be amplified in an isothermal amplification reaction by extending a cognate nucleic acid primer. In this embodiment, a signal-generating molecule of the amplifiable probe can be extendable, but need not be. A cognate nucleic acid primer contains a hybridizing sequence element that is complementary to a sequence element present on the signal-generating nucleic acid of an amplifiable probe (e.g., a complementary sequence element of a self-complementary unit or an intervening sequence element). In an isothermal amplification reaction, the signal-generating nucleic acid of an amplifiable probe hybridizes with a cognate nucleic acid primer. A cognate nucleic acid primer can be present during the reaction of an amplifiable probe with an analyte or can be added later. The hybridized cognate nucleic acid primer is extended 5' to 3' by DNA polymerase in an extension that is templated by the signal-generating nucleic acid (See FIG. 3A). Suitable temperatures for isothermal amplification do not inactivate the polymerase and include, e.g, 25° C. to 90° C., 60° C. to 80° C., 65° C. to 80° C., or 70° to 75° C. Reaction temperatures can be adjusted depending on the sequence and length of both the self-complementary unit and the primer. In addition, reaction temperatures can be adjusted based on the approximate melting temperature of a particular hybrid. Melting temperatures can be determined by a variety of computational methods known in the art, including, for example, Oligo 6.6 Molecular Biology Insights, Inc., or can be found experimentally. After extension of the cognate nucleic acid primer, the primer also can hybridize to itself and self-primed extension of the extended cognate nucleic acid primer can occur (See FIG. 3B). Self-primed extension of an extended cognate nucleic acid may yield a hairpin structure, which may in turn self-prime further extension (See FIG. 3C).

Extended nucleic acid molecules can be detected in a variety of ways. Typically, a detectably labeled nucleotide triphosphate is included in the amplification reaction mixture and is enzymatically incorporated into the extendable nucleic acid molecule during extension. The nucleotide can be radioactively labeled with an isotope such as $^{32}P$ or $^{35}S$, or can be non-radioactively labeled with a nucleotide derivative such as ChromaTide™ (Molecular Probes, Inc.). Alternatively, a non-radioactive dye that fluoresces upon binding to DNA, such as ethidium bromide (an intercalating dye), Hoescht 33258, Pico Green® (Molecular Probes, Inc., Eugene, Oreg.), SYBR® Green I (Molecular Probes, Inc., Eugene, Oreg.), and YOYO®-1 (Molecular Probes, Inc., Eugene, Oreg.) can be used to detect the extended nucleic acid molecule. These and other methods of detection are described in Capaldi et al., *Nucl Acid Res*, 28:e21 (2000) and de Silva and Wittwer, *J Chromatogr B Biomed Sci Appl*, 741:3–13 (2000).

Articles of Manufacture

Amplifiable probes described herein can be combined with packaging material and sold as a kit for detecting analytes. Components and methods for producing articles of manufacture are well known. The articles of manufacture may include an amplifiable probe and, in some embodiments, a corresponding blocked template and/or cognate nucleic acid primer. In addition, the articles of manufacture may further include reagents for detecting analytes, including nucleotide triphosphates and DNA polymerase. Instructions describing how the amplifiable probes are effective for detecting the presence of analytes may be included in such kits.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting the presence or absence of an analyte in a sample comprising:
   (a) contacting said sample with an amplifiable probe under conditions whereby said analyte, if present, binds said amplifiable probe to form a probe/analyte complex, said amplifiable probe comprising:
      (1) an analyte reactive moiety;
      (2) at least one extendable signal-generating nucleic acid, wherein each said at least one extendable signal-generating nucleic acid further comprises at least one self-complementary unit, wherein each said self-complementary unit comprises a first sequence element and a second sequence element, and wherein said first and said second nucleotide sequence elements are complementary; and
      (3) one or more linkers that connect said analyte reactive moiety to said at least one signal-generating nucleic acid;
   (b) extending said at least one extendable signal-generating nucleic acid in a reaction mixture comprising said probe/analyte complex, wherein said extendable signal-generating nucleic acid serves as its own template, wherein said extension comprises two or more cycles of extension, and wherein said extendable signal-generating nucleic acid is extended in each of said two or more cycles; and
   (c) detecting the presence or absence of said extended signal-generating nucleic acid, wherein presence of said extended signal-generating nucleic acid correlates with the presence of said analyte.

2. The method of claim 1, wherein said reaction mixture further comprises at least one nucleotide triphosphate that is detectably labeled.

3. The method of claim 2, wherein said at least one nucleotide triphosphate is labeled with a radioisotope.

4. The method of claim 2, wherein said at least one nucleotide triphosphate is labeled with a non-radioactive label.

5. The method of claim 2, wherein said at least one nucleotide triphosphate is labeled with a fluorescent label.

6. The method of claim 1, wherein a non-radioactive dye is used to detect said extended nucleic acid molecule.

7. The method of claim 1, wherein said reaction mixture further comprises an isolated nucleic acid template, said nucleic acid template comprising at least one self-complementary unit, wherein each said self-complementary unit comprises a first hybridizing sequence element and a second hybridizing sequence element, wherein said first and said second hybridizing sequence elements are complementary to each other, and wherein said nucleic acid template is blocked at its 3' and 5' termini.

8. The method of claim 7, wherein said isolated nucleic acid template comprises a phosphorothioate backbone.

9. The method of claim 1, wherein said at least extendable signal-generating nucleic acid is isothermally extended.

10. A method of detecting the presence or absence of an analyte in a sample comprising:
  (a) contacting said sample with an amplifiable probe under conditions whereby said analyte, if present, reacts with said amplifiable probe to form a modified amplifiable probe, said amplifiable probe comprising:
    (1) an analyte reactive moiety;
    (2) at least one extendable signal-generating nucleic acid, wherein each said at least one extendable signal-generating nucleic acid further comprises at least one self-complementary unit, wherein each said self-complementary unit comprises a first sequence element and a second sequence element, and wherein said first and said second sequence elements are complementary; and
    (3) one or more linkers that connect said analyte reactive moiety to said at least one signal-generating nucleic acid;
  (b) extending said at least one extendable signal-generating nucleic acid in a reaction mixture comprising said probe/analyte complex, wherein said extendable signal-generating nucleic acid serves as its own template, wherein said extension comprises two or more cycles of extension, and wherein said extendable signal-generating nucleic acid is extended in each of said two or more cycles; and
  (c) detecting the presence or absence of said extended signal-generating nucleic acid, wherein presence of said extended signal-generating nucleic acid correlates with the presence of said analyte.

11. The method of claim 10, wherein said at least extendable signal-generating nucleic acid is isothermally extended.

12. A method of detecting the presence or absence of an analyte in a sample comprising:
  (a) contacting said sample with an amplifiable probe under conditions whereby said analyte, if present, binds said amplifiable probe to form a probe/analyte complex, said amplifiable probe comprising:
    (1) an analyte reactive moiety;
    (2) at least one signal-generating nucleic acid, wherein each said at least one signal-generating nucleic acid further comprises at least one self-complementary unit, wherein each said self-complementary unit comprises a first sequence element and a second sequence element, and wherein said first and said second nucleotide sequence elements are complementary; and
    (3) one or more linkers that connect said analyte reactive moiety to said at least one signal-generating nucleic acid;
  (b) contacting said probe/analyte complex with a cognate nucleic acid primer/template;
  (c) extending said cognate nucleic acid primer/template by performing an isothermal amplification reaction in a reaction mixture comprising said probe-analyte complex, wherein said extended cognate nucleic acid primer undergoes further self-primed extension; and
  (d) detecting the presence or absence of said extended signal-generating nucleic acid, wherein presence of said extended signal-generating nucleic acid correlates with the presence of said analyte.

13. The method of claim 12, wherein said signal-generating nucleic acid is extendable.

14. The method of claim 1 wherein said analyte reactive moiety is a polypeptide.

15. The method of claim 1 wherein said analyte reactive moiety is a nucleic acid molecule.

16. The method of claim 1 wherein said analyte reactive moiety interacts with one or more polypeptides.

17. The method of claim 1 wherein said analyte reactive moiety interacts with one or more nucleic acid molecules.

18. The method of claim 1 wherein said analyte reactive moiety interacts with one or more molecules selected from the group consisting of polypeptide, nucleic acid, carbohydrate, lipid, and hapten.

* * * * *